United States Patent [19]

Welber et al.

[11] Patent Number: 4,635,632

[45] Date of Patent: Jan. 13, 1987

[54] QUICK RELEASE CONNECTOR FOR A SURGICAL DEVICE

[75] Inventors: Stanley Welber, Palatine; Nick Lakatos, DesPlaines, both of Ill.

[73] Assignee: Eder Instrument Co., Princeton, N.J.

[21] Appl. No.: 617,339

[22] Filed: Jun., 1984

[51] Int. Cl.⁴ .............................................. A61B 17/36
[52] U.S. Cl. .................................. 128/303.1; 285/283
[58] Field of Search ...................... 128/4, 6, 11, 303.1, 128/395–398, 303.15; 464/901; 403/DIG. 4; 285/283, 334.1, 393; 30/340

[56] References Cited

U.S. PATENT DOCUMENTS

| | | | |
|---|---|---|---|
| 2,951,482 | 9/1960 | Sullivan | 30/340 |
| 3,272,203 | 9/1966 | Chito | 128/303.1 |
| 3,821,510 | 6/1974 | Mancheryan | 128/303.1 |
| 4,120,293 | 10/1978 | Muckerheide | 128/395 |
| 4,132,227 | 1/1979 | Ibe | 128/11 |
| 4,437,458 | 3/1984 | Upsher | 128/11 |
| 4,473,074 | 9/1984 | Vassiliadis | 128/303.1 |

Primary Examiner—Edward M. Coven
Assistant Examiner—Max F. Hindenburg
Attorney, Agent, or Firm—McDougall, Hersh & Scott

[57] ABSTRACT

A quick release mechanism for detachably interconnecting a bronch tube with a laser micromanipulator. The bronch tube is provided with a channel aligned transversely to the tube axis and opening downwardly at an angle of approximately 45 degrees. The micromanipulator bracket includes a complementary pin adapted to receive the bronch tube channel thereon and to guide and position the tube in proper orientation. The micromanipulator bracket further includes an externally threaded barrel and bevelled locking nut which is threaded downwardly onto the bronch tube thereby locking the bronch tube against the bracket pin.

4 Claims, 4 Drawing Figures

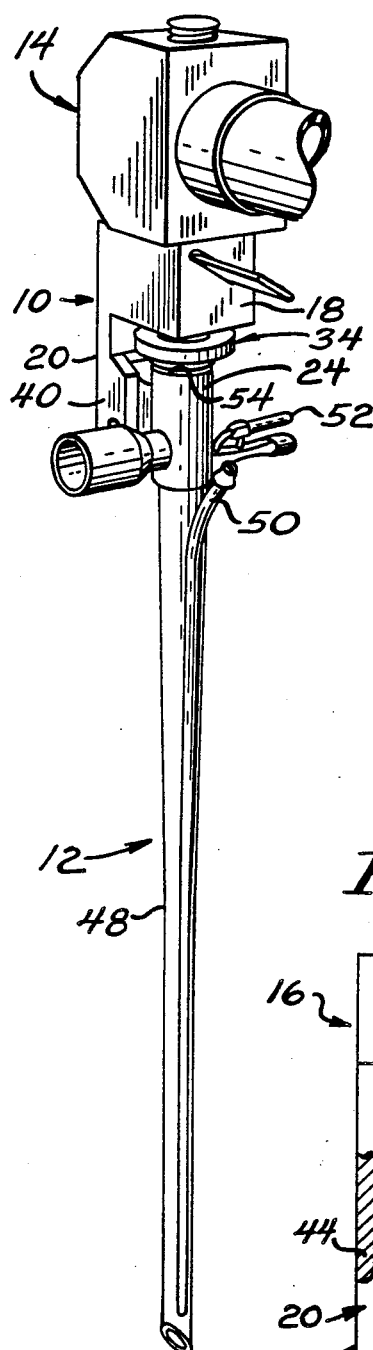
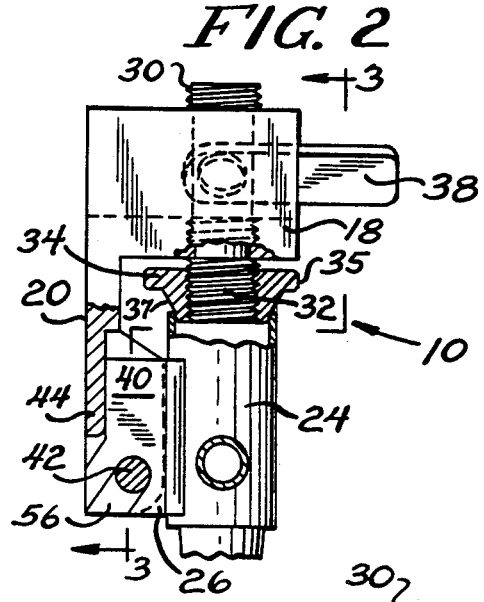
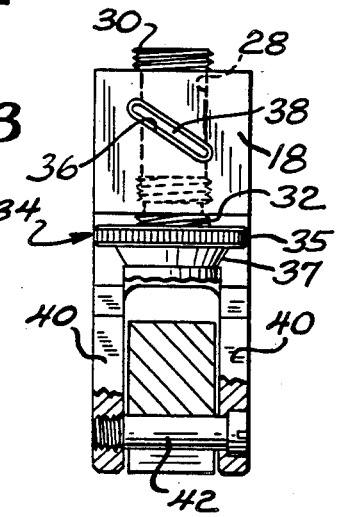
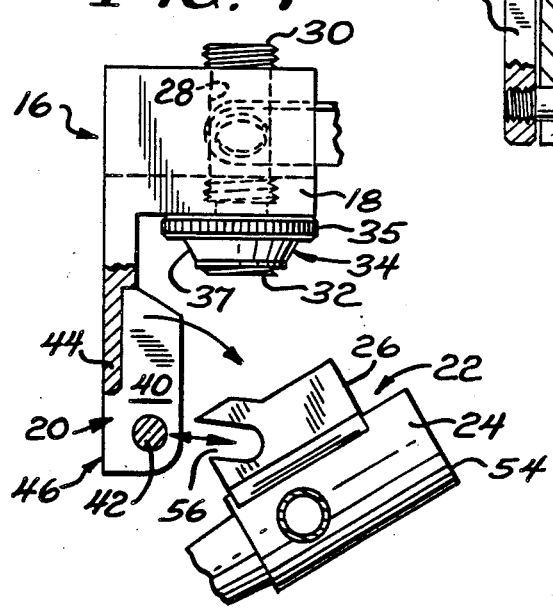

QUICK RELEASE CONNECTOR FOR A SURGICAL DEVICE

The present invention relates generally to laser surgical apparatus and, more specifically, to a quick disconnect mechanism for the interconnection of a bronch tube to the end of a laser micromanipulator arm.

A variety of laser surgical procedures are now known in which a precision micromanipulator is utilized to direct the focused laser energy onto human tissue. The present apparatus is particularly suited to one such procedure wherein a surgical device known as a 'bronch tube' (named for its intended functional insertion into the human bronchial tube) is positioned and locked in rigid fixed relationship to the micromanipulator arm. It will be appreciated that throughout any given operative procedure, it is often necessary to replace the bronch tube, or similar instrument, for cleaning or to substitute an instrument of differing dimensions or characteristics. The quick release mechanism disclosed herein facilitates the rapid connection or exchange of bronch tubes in an apparatus which simultaneously maintains accurate axial alignment of the bronch tube on the micromanipulator arm to assure proper projection of the focused laser beam through the relatively narrow neck of the bronch tube.

The present quick release connector includes a generally L-shaped mounting bracket defining a main body portion containing an externally threaded barrel member and an arm member having an alignment pin oriented generally transverse to the axis of the bronch tube and laser beam therethrough. The bronch tube includes a complementary transverse slot opening generally downwardly adapted to receive the pin member thereby forming hinge-like structure facilitating the pivotal rotation of the bronch tube into proper axial alignment. The pin further functions as a stop against which the bronch tube slot rests when the tube is locked into position. Locking of the bronch tube is achieved by advancing a knurled nut, which is threaded onto the barrel member, downwardly into contact with the upper opening or aperture of the bronch tube thereby forcing and locking the bronch tube against the arm member pin. The bottom of the nut is preferably bevelled thereby urging the bronch tube into proper symmetric orientation about the micromanipulator center axis.

It is therefore an object of the present invention to provide a quick release mechanism for bronch tubes or similar surgical instruments permitting such instruments to be quickly and effortlessly installed on, and removed from, a laser micromanipulator arm. It is a further object that the present mechanism shall provide for the rigid retention of the instrument and shall effect the requisite axial alignment whereby the laser beam may be propagated through the instrument for projection onto human tissue. The alignment shall be automatically achieved upon the locking engagement of the instrument onto the micromanipulator arm without special or additional alignment steps. These and other objects will be apparent from the accompanying figures and written specification.

FIG. 1 is a perspective view of the bronch tube quick release mechanism of the present invention shown on the end of a micromanipulator arm;

FIG. 2 is a left side view, partially in section, of the quick release mechanism of FIG. 1 showing details of the pin and slot and bevelled barrel nut;

FIG. 3 is a frontal sectional view taken substantially along line 3—3 of FIG. 2; and FIG. 4 is a left side view of the present quick release mechanism illustrating the release and removal of the bronch tube.

DESCRIPTION OF THE PREFERRED EMBODIMENT

Referring to FIG. 1, the quick release mechanism 10 of the present invention is shown rigidly locking a bronch tube 12 in proper axial alignment below the instrument end of micromanipulator 14. As best shown in FIG. 4, release mechanism 10 is comprised of an L-shaped bracket 16, defined by an upper main body portion 18 and a downwardly extending arm 20, and a mating bronch tube connect member 22, defined by a cylindrical collar 24 and slotted block 26 rigidly affixed thereto.

A threaded bore 28, disposed vertically through the body portion of bracket 16, passes the laser energy from the micromanipulator 14 to the bronch tube 12 and, further, receives threaded upper and lower bushings 30 and 32, respectively. Upper bushing 30 is threaded into the micromanipulator 14 thereby to rigidly mount the bronch tube and quick release mechanism therebelow while lower bushing 32 receives the bevelled locking nut 34 for axial movement therealong. Nut 34 preferably includes a knurled annular ring 35, adapted to aid hand rotational manipulation of the nut, and a bevelled conical surface 37 adapted, as detailed further below, to lock the bronch tube in proper axial alignment. A diagonal slot 36 is provided in the bracket body to receive an optically transparent split window 38. Spit window 38 functions in the conventional manner to block the undesired upward travel and entry of moisture into the micromanipulator.

The bracket arm 20 is integrally formed with the main bracket body 18 and includes a pair of parallel spaced sidewalls 40 into which a hinge and locking pin 42 is threadably received. As explained in more detail below, pin 42 functions in combination with the bevelled nut 34 to position and secure the bronch tube in proper alignment within the bracket 16. The rear wall 44 of the bracket arm terminates above the level of pin 42 thereby defining an unobstructed opening 46 between sidewalls 40 and adjacent pin 44 into which the slotted block of the bronch tube may enter without interference.

The bronch tube 12 is defined by a generally conventional tapered member 48 facilitating the required access to the patient's internal organ or tissue structure. More specifically, a suction port 50 is provided in the tube through which excess liquid matter may be removed and, further, the tube includes a fiber optical light port 52 adapted to permit ongoing visual feedback during the operative procedure. Finally, rigidly attached to the upper end of the tapered bronch tube is the connect member 22 which, as previously indicated, serves to removably interconnect the the bronch tube with the mating bracket 16 and micromanipulator 14. The laser beam projected through the micromanipulator 14 enters bronch tube 12 through connect member collar 24 and, in turn, travels through the tapered member 48.

The collar 24 of the bronch tube connect member 22 defines a circular upper edge 54 adapted, as explained below, to seat on the bevelled locking nut 34 as the nut is advanced downwardly into locking engagement of the bronch tube. The slotted block 26 of the connect member is rigidly attached to the collar 24, by welding or otherwise, and is provided with a channel or slot 56 generally transverse to the longitudinal bronch tube axis and opening downwardly at approximately a 45 degree angle thereto. This slot is adapted for pivotal and locking engagement with bracket pin 42 as outlined below.

It will be appreciated that the relatively slender contour of tapered member 48 of the bronch tube requires precise alignment with reference to the micromanipulator and the beam projected therefrom in order that the laser beam be properly directed through the bronch tube and, ultimately, into contact with the selected tissue area. In particular, it is necessary that the axis of the bronch tube be aligned along the laser output axis of the micromanipulator. To assure proper axial alignment when the bronch tube is retained within the quick release mechanism of the present invention, slot 56 is dimensioned such that the center axis of pin 42, when fully received within the slot, is spaced equally from the center axes of bracket bushing 32 and bronch tube 12.

Quick connect and release operation of the present invention is best illustrated by reference to FIG. 4 wherein the bronch tube connect member 22 is depicted in either its initial entry or its final release orientation. Assuming the former, engagement of the bronch tube is accomplished by orienting the bronch tube with slot 56 opening generally toward bracket pin 42; moving the bronch tube to the left until pin 42 is fully received in slot 56; then, pivoting the bronch tube on pin 42 in a counterclockwise direction into a generally vertical position with the circular upper edge 54 of collar 24 generally adjacent and below bushing 32 and nut 34. The nut 34 is thereafter advanced downwardly in conventional threaded fashion causing its bevelled lower surface 37 to enter collar 24. As the nut is further advanced, the bevelled surface centers collar 24 thereby axially aligning the bronch tube and bushing 32 and, further, urging the bronch tube downwardly into rigid locking engagement on bracket pin 42.

Removal of the bronch tube is achieved as simply by reversing the above described steps wherein the locking nut 34 is threaded upwardly on bushing 32 until fully clear of collar 24; the bronch tube is pivoted clockwise generally in the orientation depicted in FIG. 4; then, withdrawn to the right until fully released from bracket 16.

Thus, the present invention provides for the rapid, effortless interconnection and release of a surgical bronch tube or other surgical instrument. Importantly, the present structure achieves the desired engagement and release while simultaneously maintaining axial alignment of the narrow surgical instrument along the laser output axis from the micromanipulator. It will be appreciated that while the present invention has been described with reference to a surgical bronch tube that it has application for the quick connection and release of other instruments particularly where the maintenance of axial alignment between the instrument and its source head is required.

What is claimed:

1. A quick release device for detachably connecting a surgical instrument to a surgical output apparatus such as a laser micromanipulator including a first member, the first member having bushing means extending therefrom and a nut means on the bushing means, means for advancing the nut means axially along the bushing means, pin means rigidly affixed to the first member, means for attaching the first member to the output apparatus; a second member connected to the surgical instrument, the second member having a slot means for receiving the first member pin means for relative pivotal movement between the first and second members, nut receiving means on the second member whereby the surgical instrument may be detachably connected to the output apparatus by advancing the nut means into abutment with the nut receiving means thereby urging the pin and slot means into tight engagement.

2. A quick release device for detachably connecting and aligning a surgical instrument to a surgical output apparatus such as a laser micromanipulator, the surgical instrument defining a working axis and the output apparatus defining an output axis, the quick release device including a first member, the first member having bushing means extending therefrom and a nut means on the bushing means, means for moving the nut means axially along the bushing means, the bushing means defining a bushing axis, pin means rigidly affixed to the first member, means for attaching the first member to the output apparatus such that the respective output and bushing axes are in axial alignment a second member connected to the surgical instrument, the second member including a generally cylindrical collar means having a collar axis coinciding with the instrument working axis, the second member having slot means for receiving the first member pin means for relative pivotal movement between the first and second members, nut receiving means on the second member whereby the surgical instrument may be detachably connected to the output apparatus by advancing the nut means into abutment with the nut receiving means thereby axially aligning said output apparatus and surgical instrument axes.

3. The quick release device of claim 2 wherein the nut means defines a generally bevelled contour facing the second member collar means and the collar means includes a generally circular edge comprising said nut receiving means whereby the collar and surgical instrument axis is brought into axial alignment with the bushing and output axis as the bevelled contour of the nut means is advanced along the bushing means into engagement with the circular edge of the collar means.

4. A quick release device for detachably connecting and aligning surgical instrument to a surgical output apparatus such as a laser micromanipulator, the surgical instrument defining a working axis and the output apparatus defining an output axis; the quick release device including a first connector member defining a body portion and an arm portion; a bore extending through the body portion defining a first member axis; means for attaching the first member body portion to the output apparatus whereby said respective first member and output axes coincide; a bushing extending from the body portion bore in axial alignment therewith; the arm portion defining a longitudinal axis oriented generally parallel to the bore and bushing axis and extending from the body portion in the same direction as the bushing; a pin means rigidly affixed to the arm portion, the pin means having an axis disposed generally perpendicular to a plane defined by the arm portion and bushing axes; a nut received on the bushing for axial movement thereon, the surface of the nut facing along the bushing axis away from the body portion defining an annular bevelled contour; the quick release device further including a second connector member defining a generally cylindrical collar portion attached to the instrument such that the collar portion and instrument working axes coincide; the collar portion having a generally circular nut receiving edge; the second connector member including pin engagement means, said means generally defining a channel in the second connector member transversely oriented to the collar axis, the channel opening away from the collar axis and nut receiving edge whereby the second connector member channel may be positioned on the first connector member pin and the first connector member nut advanced into engagement with the second connector member nut receiving edge thereby locking the instrument in proper axial alignment to the output apparatus.

* * * * *